(12) United States Patent
Redmond et al.

(10) Patent No.: US 10,299,837 B2
(45) Date of Patent: May 28, 2019

(54) SACROILIAC JOINT STABILIZATION AND FIXATION DEVICES AND RELATED METHODS

(71) Applicant: West End Bay Partners, LLC, Tyler, TX (US)

(72) Inventors: Andy J. Redmond, Tyler, TX (US); Charles R. Gordon, Tyler, TX (US); Erik Wagner, Austin, TX (US)

(73) Assignee: West End Bay Partners, LLC, Tyler, TX (US)

( * ) Notice: Subject to any disclaimer, the term of this patent is extended or adjusted under 35 U.S.C. 154(b) by 0 days.

(21) Appl. No.: 15/453,778

(22) Filed: Mar. 8, 2017

(65) Prior Publication Data

US 2017/0258498 A1 Sep. 14, 2017

Related U.S. Application Data

(60) Provisional application No. 62/305,404, filed on Mar. 8, 2016, provisional application No. 62/347,981, filed on Jun. 9, 2016.

(51) Int. Cl.
*A61B 17/70* (2006.01)
*A61B 17/86* (2006.01)
*A61B 17/84* (2006.01)

(52) U.S. Cl.
CPC ........ *A61B 17/7055* (2013.01); *A61B 17/844* (2013.01); *A61B 17/863* (2013.01); *A61B 17/8685* (2013.01); *A61B 2017/8655* (2013.01)

(58) Field of Classification Search
CPC .......... A61F 2/30988; A61F 2002/3041; A61F 2002/30512; A61F 2002/30514;
(Continued)

(56) References Cited

U.S. PATENT DOCUMENTS 5,522,899 A 6/1996 Michelson
5,693,100 A * 12/1997 Pisharodi .............. A61F 2/4455
623/17.16

(Continued)

OTHER PUBLICATIONS

"Sacroiliac (SI) Joint Fusion Technique," *SPINEMarketGroup*, Apr. 19, 2016 [http://www.thespinemarketgroup.com/si-joint-fusion/; Accessed: Apr. 25, 2016].
(Continued)

*Primary Examiner* — Kevin T Truong
*Assistant Examiner* — David C Comstock
(74) *Attorney, Agent, or Firm* — Norton Rose Fulbright US LLP

(57) ABSTRACT

An anchor device for use in sacroiliac joint stabilization comprises a housing having a bore, one or more apertures, and a threaded outer surface, one or more engagement members at least partially disposed in the housing, where at least one of the one or more engagement members is movable between a retracted position and an extended position such that, when the at least one of the one or more engagement members is in the extended position, the at least one of the one or more engagement members extends through at least one of the one or more apertures, and where, when the at least one of the one or more engagement members is in the extended position, the at least one of the one or more engagement members is configured to engage a cortical wall of a sacrum bone.

7 Claims, 13 Drawing Sheets

(58) Field of Classification Search
CPC .. A61F 2002/30579; A61F 2002/30622; A61F 2002/30904; A61F 2002/30995; A61B 17/7055; A61B 17/863; A61B 17/8685; A61B 2017/8655
USPC .............. 606/246, 301, 310, 317, 321, 279; 623/17.11, 17.16
See application file for complete search history.

(56) References Cited

U.S. PATENT DOCUMENTS

| | | | |
|---|---|---|---|
| 7,828,848 B2* | 11/2010 | Chauvin | A61F 2/4455 606/313 |
| 8,187,332 B2 | 5/2012 | McLuen | |
| 8,551,171 B2 | 10/2013 | Johnson et al. | |
| 8,562,651 B2 | 10/2013 | Metcalf et al. | |
| 8,900,279 B2 | 12/2014 | Assell et al. | |
| 8,986,348 B2 | 3/2015 | Reiley | |
| 9,089,371 B1 | 7/2015 | Faulhaber | |
| 2002/0022887 A1* | 2/2002 | Huene | A61F 2/446 623/17.16 |
| 2011/0319946 A1* | 12/2011 | Levy | A61B 17/7035 606/309 |
| 2013/0245703 A1 | 9/2013 | Warren et al. | |
| 2015/0012051 A1 | 1/2015 | Warren et al. | |
| 2015/0313720 A1 | 11/2015 | Lorio | |

OTHER PUBLICATIONS

"Silex Sacroiliac Joint Fusion System," *X-Spine Product Guide*, Miamisburg, OH: 2013.
"Silex: Sacroiliac Joint Fusion System," *X-Spine*, [http://x-spine.com/surgeons/sacroiliac-joint/silex/; Accessed Oct. 8, 2015].
"Zyga SImmetry Patient Animation" [https://www.youtube.com/watch?v=ynQE5kIU98c; Accessed Aug. 4, 2017].
Faruqi, Omar, "Life Spine Announces Limited Release Simpact Sacroiliac Joint Fixation System," Press Release. Huntley, IL., Oct. 6, 2015.
Globus Medical SI-LOK Sacroiliac Joint Fixation System [http://si-lok.globusmedical.com/; Accessed Aug. 4, 2017].
LifeSpine SImpact Sacroiliac Joint Fixation System [https://lifespine.com/simpact/; Accessed Aug. 4, 2017].
Linhardt, Matt. "CoreLink Releases the Entasis SI Joint Fusion System" *BusinessWire*, St. May 3, 2016.
SI-Bone iFuse Implant System [https://si-bone.com/patients/ifuse-implant-system/; Accessed Aug. 4, 2017].
Substantial Equivalence Determination issued by the Food and Drug Administration for, 510(k) No. K152237, "The Entasis Dual-Lead Sacroiliac Implant," issued Feb. 4, 2016.
Twork et al., "Fixating on Innovation: A Revolutionary in Spinal Fusion Surgery," *Medical Design Briefs*, Mar. 2017.
Zimmer TriCor Sacroiliac Joint Fusion System [http://www.zimmer.com/medical-professionals/products/spine/tricor-sacroiliac-joint-fusion-system.html; Accessed Aug. 4, 2017].

* cited by examiner

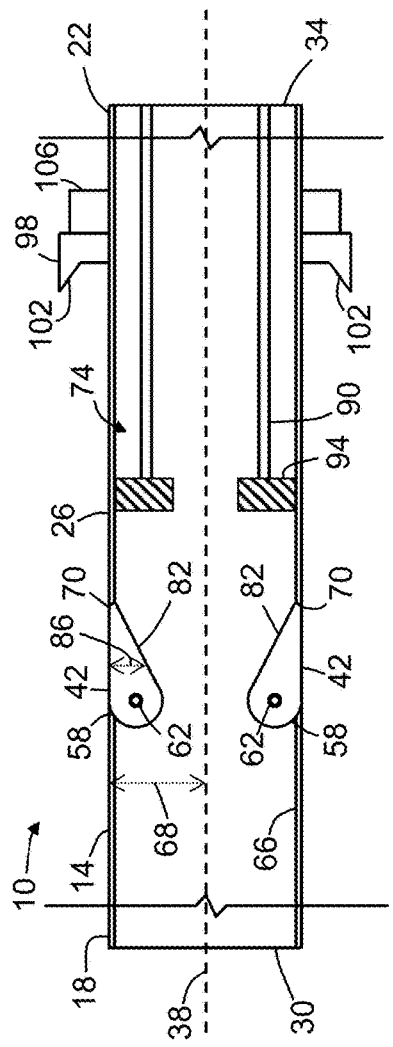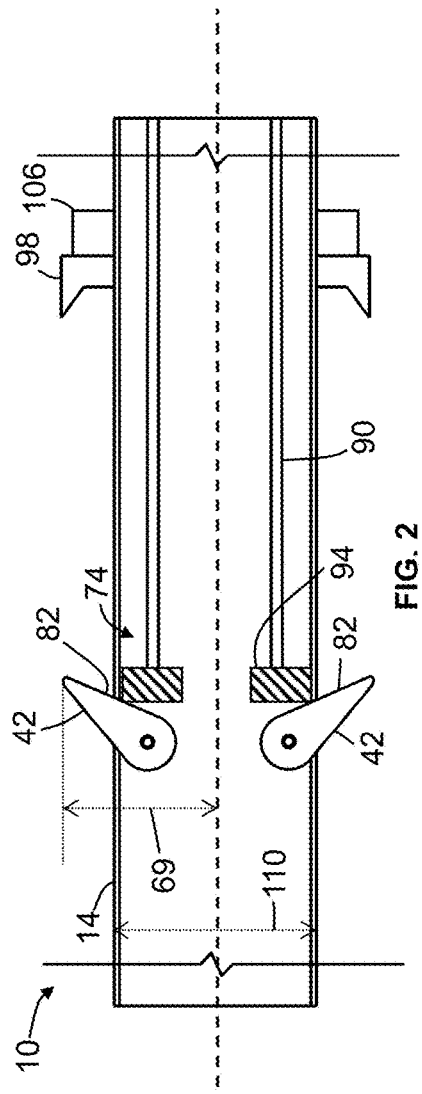

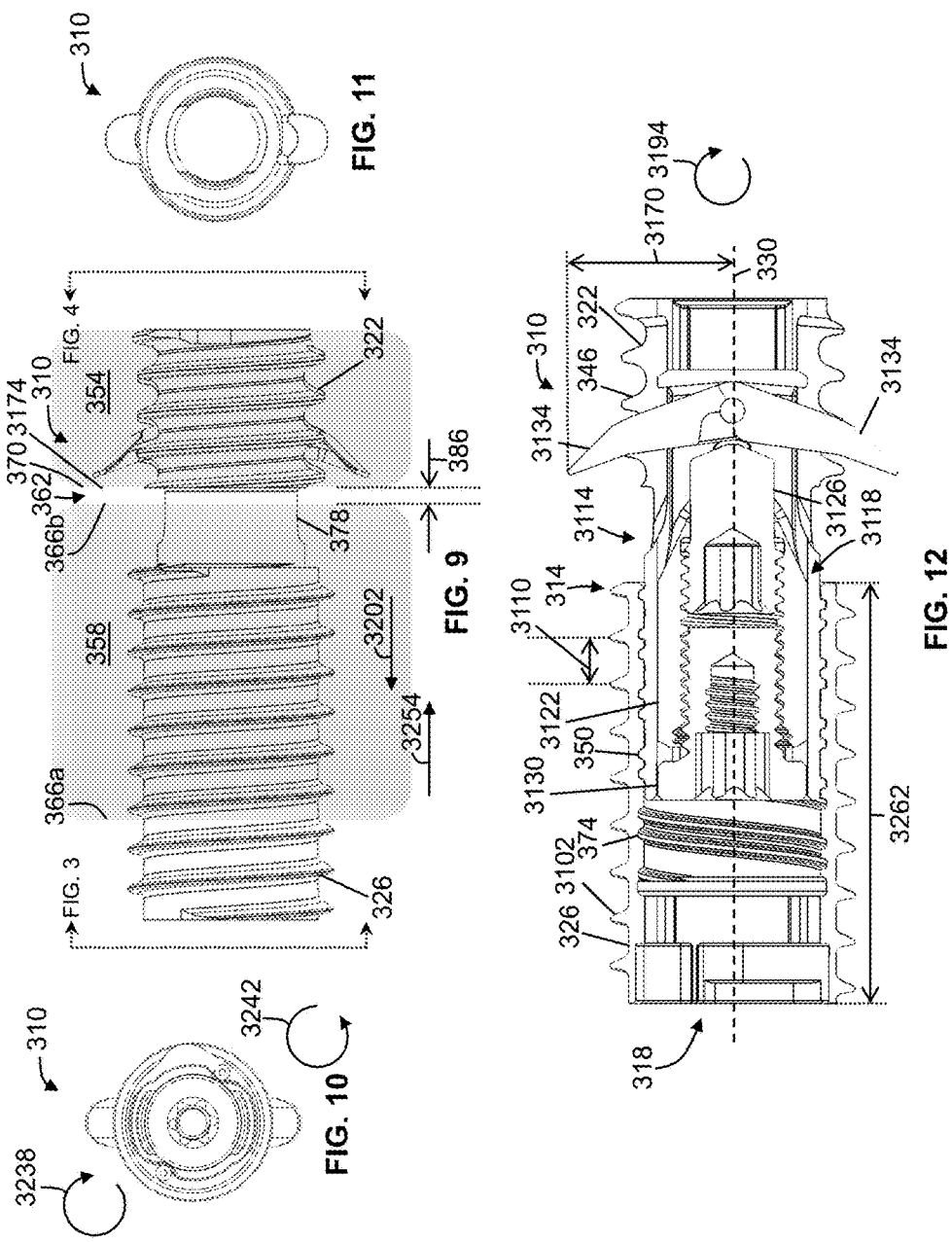

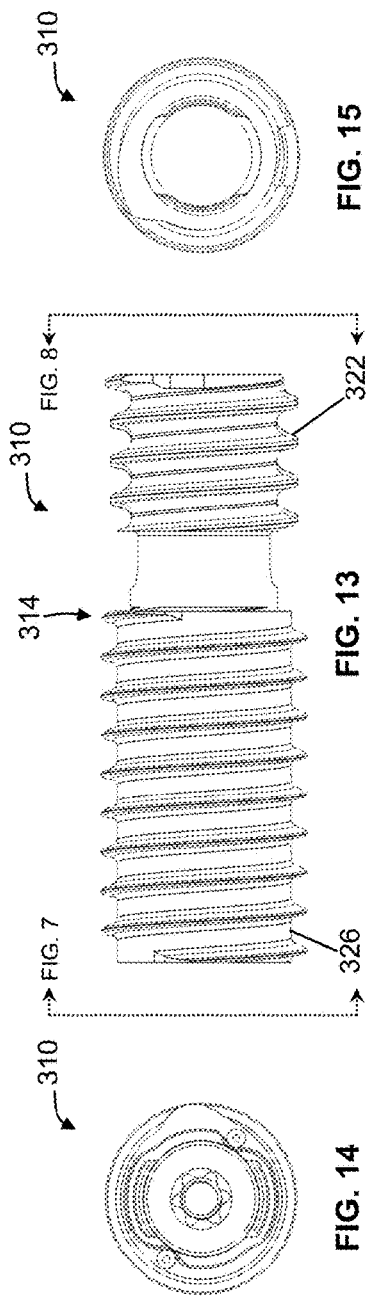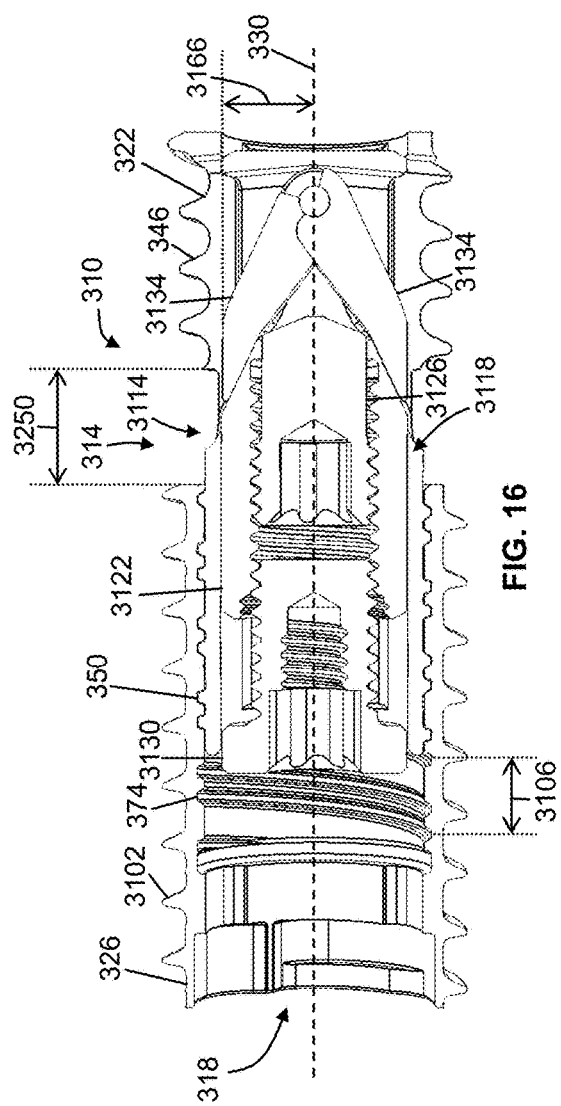

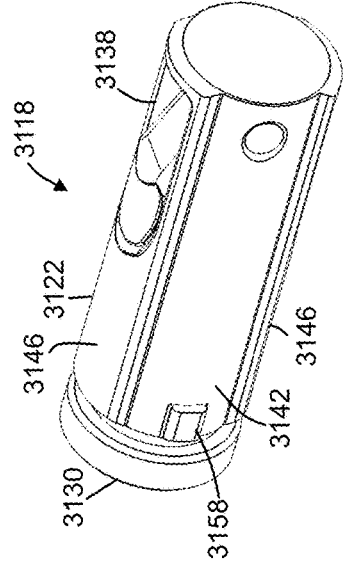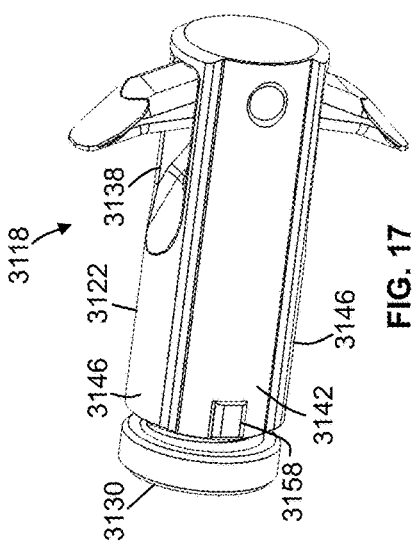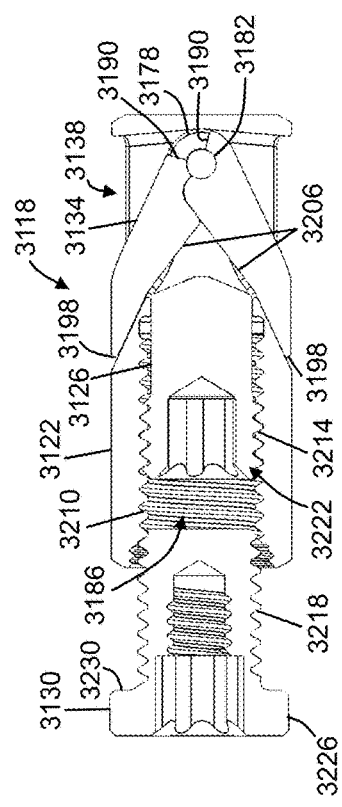

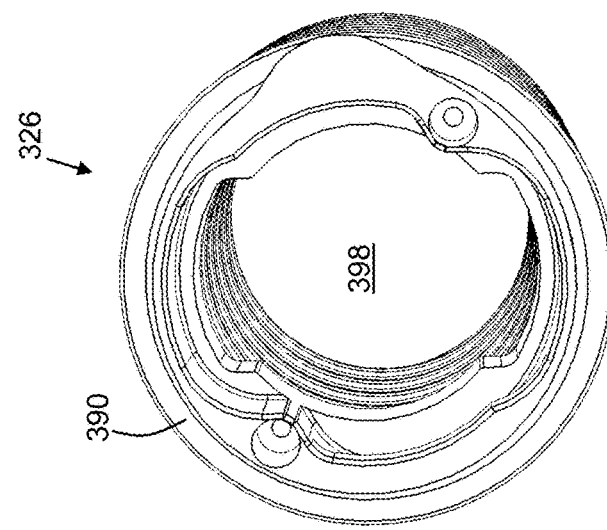
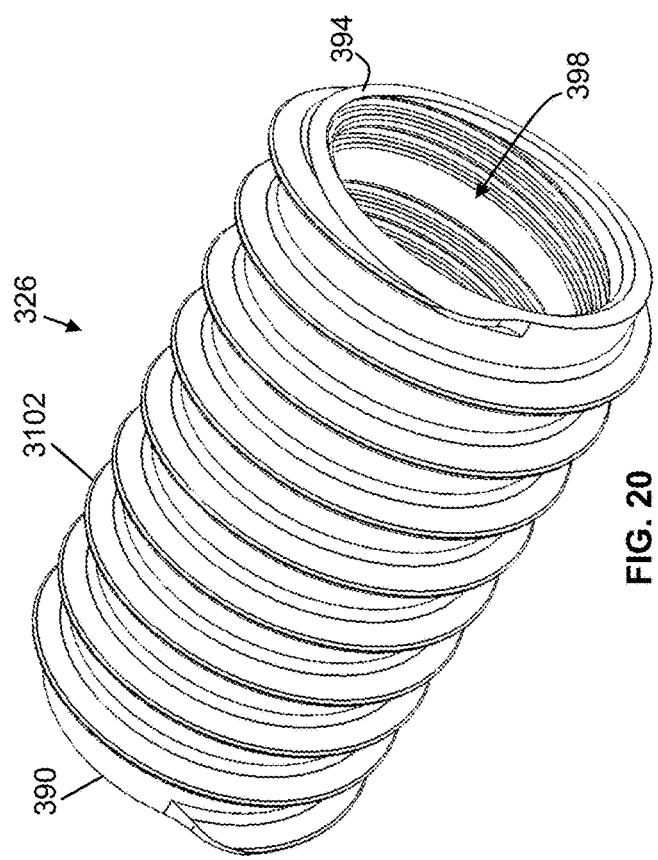

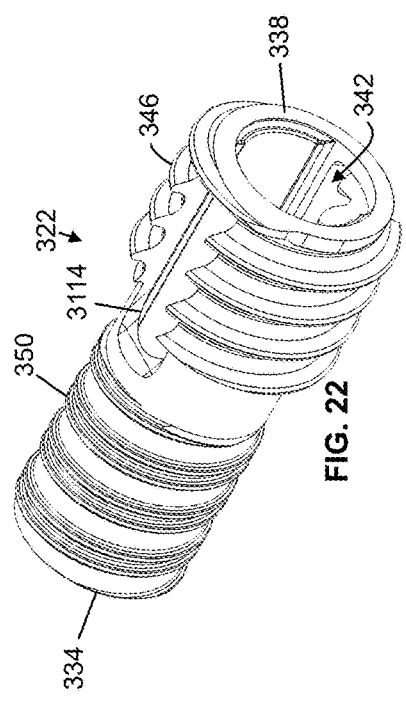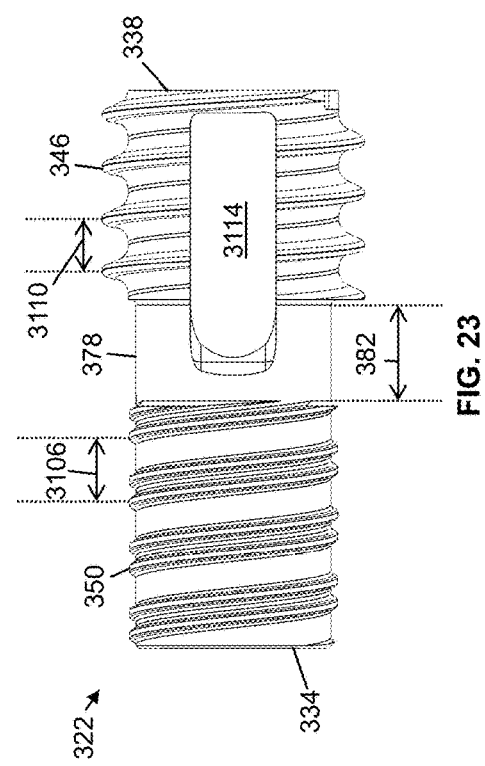

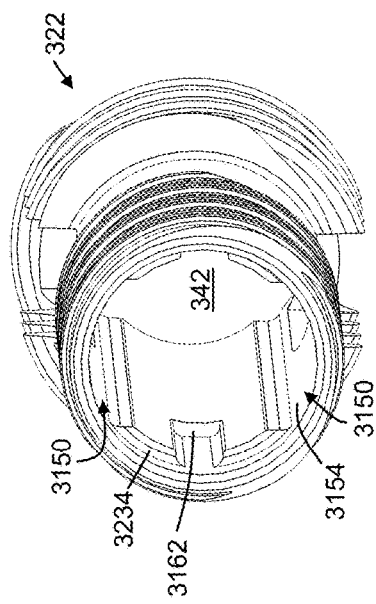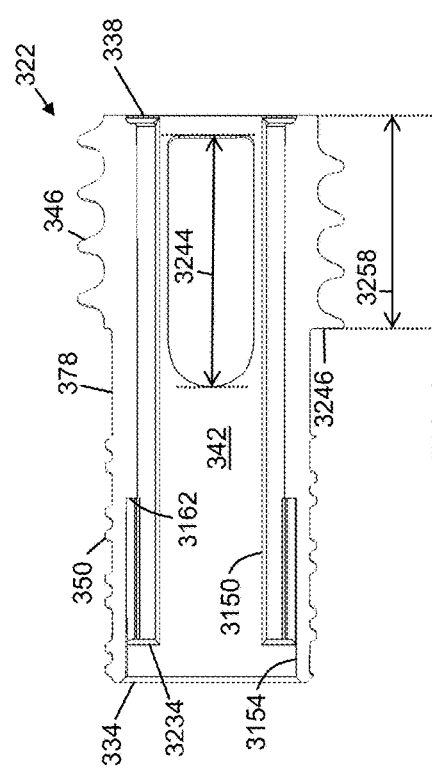

SACROILIAC JOINT STABILIZATION AND FIXATION DEVICES AND RELATED METHODS

CROSS-REFERENCE TO RELATED APPLICATIONS

This application claims priority to U.S. Provisional Application Nos. 62/305,404, filed on Mar. 8, 2016 and Ser. No. 62/347,981, filed on Jun. 9, 2016, the entire contents of which are specifically incorporated by reference herein without disclaimer.

BACKGROUND OF THE INVENTION

1. Field of the Invention

The present invention relates generally to joint fixation devices, and more particularly, but not by way of limitation, to sacroiliac joint fixation devices and related methods.

2. Description of Related Art

The sacroiliac joint is a strong, weight-bearing synovial joint and part of the pelvis. The joint is comprised of strong ligamentous attachments and two articular dense cortical surfaces: the sacrum and the ileum. The body of both the sacrum and the ileum consists of soft cancellous bone.

The sacroiliac joint has been identified as a source of pain and disability in a large number of patients. Pain of the sacroiliac joint may be a result of bone degeneration, fracture, dislocation, and/or trauma. Current treatment management options include sacroiliac joint fusion. Traditional open surgical techniques for sacroiliac joint fusion carry a significant risk for complications. Percutaneous sacroiliac joint fusion, however, has emerged as a minimally invasive option for treating sacroiliac joint pain. Most percutaneous sacroiliac joint fixation techniques include passing a Kirschner wire ("K-wire") or Steinmann pin through the ilium into the sacrum via a lateral approach, followed by bone site preparation and placement of one or more fixation devices. These fixation devices may include a variety of longitudinal screws and/or triangular implants that are configured to be passed across the sacroiliac joint and anchored into the soft cancellous bone of the sacrum. Thereafter, bone graft may be placed into the sacroiliac joint to promote fusion.

A disadvantage, however, of these devices is the reliance on screw thread fixation and/or a simple compression fit in the soft cancellous bone of the sacrum. Therefore, there remains a need for sacroiliac joint stabilization fixation devices with improved sacral anchoring to provide better long-term compression of the joint space.

SUMMARY OF THE INVENTION

This disclosure includes embodiments of anchor devices and methods of using anchor devices that comprise an expandable engagement member configured to engage a sacroiliac joint.

Some embodiments of the present anchor devices for use in sacroiliac joint stabilization comprise: an elongated housing; an engagement member at least partially disposed in a bore of the housing, where the engagement member is movable between a retracted position and an extended position; an actuator movable in the bore of the housing and configured to effectuate movement of the engagement member between the retracted position and the extended position; a washer movable along an outer surface of the housing toward the engagement member; and a locking nut movable along the outer surface of the housing, where the locking nut is configured to urge the washer toward the engagement member.

In some embodiments of the present devices, the actuator is movable relative to the housing and configured to engage the engagement member in order to effectuate movement of the engagement member between the retracted position and the extended position.

In some embodiments of the present devices, the actuator includes an expansion nut configured to mate with a threaded inner surface of the housing and configured to engage the engagement member to effectuate movement between the retracted position and the extended position.

In some embodiments of the present devices, the expansion nut is configured to engage a tapered surface of the engagement member to effectuate movement between the retracted position and the extended position.

In some embodiments of the present devices, the engagement member is rotatable via a hinge between the retracted position and the extended position.

In some embodiments of the present devices, the engagement member is longitudinally fixed relative to the housing.

In some embodiments of the present devices, the washer includes a plurality of protrusions on a side facing the engagement member.

In some embodiments of the present devices, the engagement member is biased toward the retracted position by a biasing member.

Some embodiments of the present methods (e.g., of using an anchor device to stabilize a sacroiliac joint) comprise: inserting a guidewire across a sacroiliac joint (SI joint), such that the guidewire at least partially extends into a sacrum and an ilium; positioning an anchor device across the SI joint such that the device at least partially extends into the sacrum and the ilium, where the anchor device includes: an elongated housing, an engagement member at least partially disposed in a bore of the housing, where the engagement member is movable between a retracted position and an extended position, an actuator movable in the bore of the housing and configured to effectuate movement of the engagement member between the retracted position and the extended position, where in the extended position, the engagement member is configured to engage an inner surface of a cortical wall of the sacrum, and a locking nut longitudinally movable along an outer surface of the housing toward the engagement member; moving the actuator in the bore of the housing toward the engagement member; engaging the actuator with the engagement member, thereby moving the engagement member from the retracted position towards the extended position; and moving the locking nut toward the engagement member, thereby providing rigid fixation of the SI joint.

In some embodiments of the present devices, when the anchor device is positioned across the SI joint, the engagement member is longitudinally spaced from the inner surface of the cortical wall of the sacrum by a distance such that the engagement member is movable towards the extended position.

In some embodiments of the present devices, engaging the actuator with the engagement member includes engaging a tapered surface of the engagement member.

In some embodiments of the present devices, the engagement member is configured to taper from a first end towards a second end, and where the second end is configured to engage the inner surface of the cortical wall of the sacrum.

Some embodiments of the present methods further comprise engaging a washer against an outer surface of a cortical wall of the ilium, where the washer is movable along the outer surface of the housing toward the engagement member.

Some embodiments of the present methods further comprise fastening the washer against the outer surface of the cortical wall of the ilium using the locking nut.

In some embodiments of the present devices, the actuator includes an expansion nut configured to mate with a threaded inner surface of the housing and configured to engage the engagement member to effectuate movement between the retracted position and the extended position.

In some embodiments of the present devices, the expansion nut is coupled to a rotatable shaft and the method further comprises rotating the shaft, thereby moving the actuator towards the engagement member.

Some embodiments of the present methods further comprise moving the actuator longitudinally away from the engagement member, thereby causing the engagement member to move toward the retracted position.

Some embodiments of the present anchor devices for use in sacroiliac joint stabilization comprise: an elongated housing having a first anchor portion axially movable relative to a second anchor portion; an engagement member at least partially disposed in a bore of the first anchor portion, where the engagement member is deformable from a retracted position and an extended position, and where in the extended position at least a portion of the engagement member extends through an aperture defined by the housing; and an actuator movable in the bore of the housing and configured to engage the engagement member such that the engagement member deforms from the retracted position to the extended position.

Some embodiments of the present anchor devices for use in sacroiliac joint stabilization comprise: an elongated housing having a first channel and a first aperture; a carriage assembly disposable in the first channel, the carriage assembly comprising: a carriage housing having a second channel and a second aperture, an engagement member movable between a retracted position and an extended position, and an actuation member movable in the second channel and configured to effectuate movement of the engagement member between the retracted position and the extended position; and where the second aperture is configured to be axially and circumferentially aligned with the first aperture such that the engagement member extends through both the first aperture and the second aperture when the engagement member is in the extended position.

Some embodiments of the present anchor devices for use in sacroiliac joint stabilization comprise: a first anchor having an outer thread and an inner thread; a second anchor movable relative to the first anchor, where the second anchor includes an outer thread configured to mate with the inner thread of the first anchor, where a pitch of the inner thread of the first anchor is greater than a pitch of the outer thread of the first anchor; and a carriage assembly disposable in the second anchor, the carriage assembly comprising: an engagement member movable between a retracted position and an extended position, and an actuation member configured to effectuate movement of the engagement member between the retracted position and the extended position.

Some embodiments of the present methods (e.g., of using an anchor device to stabilize a sacroiliac joint) comprise: positioning an elongated housing across a sacroiliac joint (SI joint) such that the elongated housing at least partially extends into a sacrum and an ilium, where the elongated housing includes a first anchor and a second anchor; inserting a carriage assembly into the elongated housing, the carriage assembly comprising: an engagement member movable between a retracted position and an extended position, and an actuation member; engaging the actuation member with the engagement member, thereby moving the engagement member from the retracted position toward the extended position; and moving the first anchor relative to the second anchor, thereby urging the engagement member against a cortical wall of the sacrum.

Some embodiments of the present anchor devices for use in sacroiliac joint stabilization comprise: a housing having: a bore; one or more apertures; and a threaded outer surface; one or more engagement members at least partially disposed in the housing, where at least one of the one or more engagement members is movable between a retracted position and an extended position such that, when the at least one of the one or more engagement members is in the extended position, the at least one of the one or more engagement members extends through at least one of the one or more apertures; and where, when the at least one of the one or more engagement members is in the extended position, the at least one of the one or more engagement members is configured to engage a cortical wall of a sacrum bone.

Some embodiments of the present anchor devices comprise an actuator movable in the bore of the housing and configured to effectuate movement of the at least one of the one or more engagement members between the retracted position and the extended position.

In some embodiments of the present devices, the actuator is configured to engage the at least one of the one or more engagement members in order to effectuate movement of the at least one of the one or more engagement members between the retracted position and the extended position. In some embodiments of the present devices, the actuator is configured to mate with a threaded inner surface of the housing. In some embodiments of the present devices, the actuator is configured to engage a tapered surface of the at least one of the one or more engagement members to effectuate movement between the retracted position and the extended position.

In some embodiments of the present devices, the housing comprises: a first anchor having the threaded outer surface and a threaded inner surface; and a second anchor movable relative to the first anchor, where the second anchor includes a threaded outer surface configured to mate with the threaded inner surface of the first anchor, where a pitch of the threaded inner surface of the first anchor is greater than a pitch of the threaded outer surface of the first anchor.

Some embodiments of the present anchor devices comprise: a carriage assembly disposable in the second anchor, the carriage assembly comprising: the one or more engagement members, and an actuator configured to effectuate movement of the at least one of the one or more engagement members between the retracted position and the extended position.

In some embodiments of the present devices, the pitch of the threaded inner surface the first anchor is greater than the pitch of the threaded outer surface of the first anchor.

Some embodiments of the present anchor devices comprise a washer movable over the threaded outer surface of the housing toward the one or more engagement members.

Some embodiments of the present anchor devices comprise a locking nut movable along the threaded outer surface of the housing, where the locking nut is configured to urge the washer toward the one or more engagement members.

In some embodiments of the present devices, the at least one of the one or more engagement members is rotatable via a hinge between the retracted position and the extended position.

In some embodiments of the present devices, the one or more engagement members are longitudinally fixed relative to a portion of the housing configured to extend into the sacrum bone.

Some embodiments of the present anchor devices comprise an expandable core having the one or more engagement members, where the expandable core is configured to compress such that at least one of the one or more engagement members deflects outward to the extended position.

Some embodiments of the present methods of using an anchor device to stabilize a sacroiliac joint comprise: positioning an anchor device across a sacroiliac joint (SI joint) such that the device at least partially extends into a sacrum and an ilium, where the anchor device includes: a housing having: a bore; one or more apertures; and a threaded outer surface; and one or more engagement members at least partially disposed in the bore of the housing, where at least one of the one or more engagement members is movable between a retracted position and an extended position such that, when the at least one of the one or more engagement members is in the extended position, the at least one of the one or more engagement members extends through at least one of the one or more apertures; moving an actuator in the bore of the housing toward the one or more engagement members; engaging the actuator with at least one of the one or more engagement members, thereby moving the at least one of the one or more engagement members from the retracted position to the extended position; and urging, when the at least one of the one or more engagement members is in the extended position, the at least one of the one or more engagement members against a cortical wall of a sacrum bone.

In some embodiments of the present methods, when the anchor device is positioned across the SI joint, the one or more engagement members are longitudinally spaced from the cortical wall of the sacrum by a distance such that the at least one of the one or more engagement members are movable to the extended position.

In some embodiments of the present methods, the at least one of the one or more engagement members is configured to taper from a first end to a second end, and where the second end is configured to engage the cortical wall of the sacrum.

In some embodiments of the present methods, engaging the actuator with the at least one of the one or more engagement members includes engaging the actuator with a tapered surface of the at least one of the one or more engagement members.

In some embodiments of the present methods, the housing comprises: a first anchor having the threaded outer surface and a threaded inner surface; a second anchor movable relative to the first anchor, where the second anchor includes a threaded outer surface configured to mate with the threaded inner surface of the first anchor, where a pitch of the threaded inner surface of the first anchor is greater than a pitch of the threaded outer surface of the first anchor; and wherein the method comprises: axially and/or rotationally moving the first anchor relative to the second anchor to urge the at least one of the one or more engagement members against the cortical wall of the sacrum.

In some embodiments of the present methods, moving the at least one of the one or more engagement members from the retracted position to the extended position includes deforming the at least one of the one or more engagement members.

The term "coupled" is defined as connected, although not necessarily directly, and not necessarily mechanically. Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled (or configured to be couplable) to the second structure. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the devices, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1 and 2 are cross-section views of one embodiment of the present anchor devices, shown with engagement members in a first position and a second position, respectively.

FIG. 9 is a first side view of the anchor device of FIG. 8 positioned in a sacrum bone, an iliac bone, and a sacroiliac joint between the sacrum bone and the iliac bone.

FIGS. 10-12 are a second side, a third side, and a cross-section view of the anchor device of FIG. 8, respectively.

FIGS. 13-16 are the first side, the second side, the third side, and a cross-section view of the anchor device of FIG. 8, shown with the plurality of engagement members in a second position.

FIGS. 17 and 18 are a perspective view of one embodiment of a carriage assembly of the anchor device of FIG. 8, shown with the plurality of engagement members in the first position and the second position, respectively.

FIG. 19 is a cross-section view of the carriage assembly of FIGS. 17 and 18, shown with the plurality of engagement members in the second position.

FIGS. 20 and 21 are a first perspective and second perspective view, respectively, of one embodiment of an outer anchor of the anchor device of FIG. 8.

FIGS. 22-25 is a first perspective, side, second perspective, and cross-section view, respectively, of one embodiment of an inner anchor of the anchor device of FIG. 8.

DESCRIPTION OF ILLUSTRATIVE EMBODIMENTS

Figure 3:
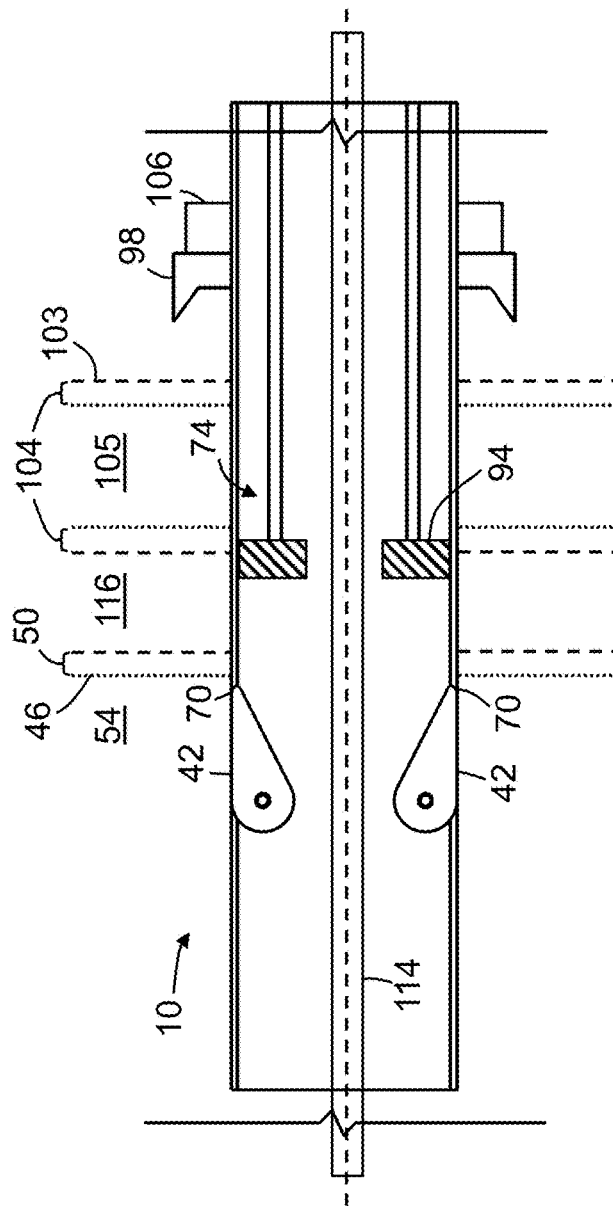
FIGS. 3 and 4 are cross-section views of the anchor device of FIGS. 1 and 2, shown disposed in a sacroiliac joint with the engagement members of FIGS. 1 and 2 in the first position and the second position, respectively.

Referring now to the drawings, and more particularly to FIGS. 1-4, shown therein and designated by the reference numeral 10 is one embodiment of the present anchor devices. In the embodiment shown, device 10 includes an elongated housing 14 (e.g., a housing) having a first end 18, a second end 22, and a midsection 26 extending between the first end and the second end. As shown, housing 14 may include a first opening 30 at first end 18 and a second opening 34 at second end 22. Housing 14 may be characterized by and described relative to a longitudinal axis 38 extending along a length of midsection 26.

In the embodiment shown, for example, in FIGS. 1-4, housing 14 may include one or more engagement members 42 (e.g., two engagement members, as shown) movable between a retracted position and an extended position, in which the engagement member is configured to securely engage an inner surface 46 of a cortical wall 50 ("sacral cortical wall") of a sacrum bone 54. More particularly, in the embodiment shown, engagement member 42 may be may be configured to be fixed along longitudinal axis 38 and rotatable between the retracted and extended positions. For example, a first end 58 of one or more engagement member(s) 42 may be coupled to a respective hinge 62 disposed at least partially in a bore 66 of housing 14 and the engagement member may be rotatable between the retracted and extended positions via the hinge. In the retracted position, an outer-most surface of engagement member 42 may be configured to extend a first distance 68 from longitudinal axis 38. In the extended position, the outer-most surface of engagement member 42 may be configured to extend a second distance 69 from longitudinal axis 38 into the cancellous bone of sacrum 54. In this embodiment, engagement member 42 may be coupled with hinge 62 such that the engagement member moves uniaxially, biaxially, or multi-axially relative to the hinge, thereby allowing the engagement member to adjust to irregularities and variable angles of sacral cortical wall 50. Housing 14 may include one or more apertures through which respective engagement members 42 are configured to extend when the engagement member(s) are in the extended position. As shown, engagement member 42 may be at least partially disposed in bore 66 of housing 14 when the engagement member is in the retracted and/or extended positions. In some embodiments, one or more engagement member(s) (e.g., 42) may be biased toward the retracted position using a biasing member such as, for example, a spring.

In the depicted embodiment, one or more engagement member(s) 42 may include any appropriate shape such that, when the engagement member is the extended position, a second end 70 of the engagement member is configured to securely engage inner surface 46 of sacral cortical wall 50 and prevent removal of housing 14 from sacrum 54 (e.g., movement in a direction 78). As shown, engagement member 42 may include an inwardly-facing tapered surface 82. For example, engagement member 42 includes a thickness 86 (e.g., measured in a direction perpendicular to longitudinal axis 38) configured to decrease from first end 58 of engagement member 42 to second end 70 of the engagement member. As shown, second end 70 of engagement member 42 can converge to a point such that the second end engages inner surface 46 of sacral cortical wall 50 (e.g., without penetrating the sacral cortical wall) to secure device 10 in sacrum 54. In some embodiments, a second end (e.g., 70) of an engagement member (e.g., 42) may include any suitable shape such that the second end engages an inner surface (e.g., 46) of a sacral cortical wall (e.g., 50) (e.g., without penetrating the sacral cortical wall) to secure a device (e.g., 10) in a sacrum (e.g., 54). As shown, when engagement member 42 is in the retracted position, the engagement member may be configured to be substantially flush with an outer surface of housing 14.

In this embodiment, housing 14 may be configured to accommodate an actuator 74, which is configured to effectuate movement of one or more of engagement member(s) 42 between the retracted position and/or the extended positions. More specifically, actuator 74 may be longitudinally movable relative to engagement member 42, such that the actuator is configured to engage (e.g., tapered surface 82 of) the engagement member. In the depicted embodiment, a portion of housing 14, such as midsection 26, includes a threaded inner surface. In some embodiments, a majority of a length of a housing (e.g., 14) includes a threaded inner surface. Actuator 74 can comprise any suitable device configured to move engagement member 42 between the retracted and extended positions. For example, in this embodiment, actuator 74 includes a (e.g., hollow) shaft 90 coupled to a threaded expansion nut 94 that is configured to mate with the threaded inner surface of housing 14. In some embodiments, a shaft (e.g., 90) and a threaded expansion nut (e.g., 94) are integrally formed. In the depicted embodiment, actuator 74 may be longitudinally movable toward one or more engagement member(s) 42 by rotating expansion nut 94 (e.g., via rotation of shaft 90). Longitudinal movement of actuator 74 relative to housing 14 may engage the actuator (e.g., expansion nut 94) with tapered surface 82 of engagement member 42. Additional longitudinal movement (e.g., towards first end 18 of housing 14) of the actuator 74 relative to the housing may move expansion nut 94 longitudinally along tapered surface 82 of engagement member 42 (e.g., towards first end 58 of the engagement member), thereby moving (e.g., rotating) the engagement member from the retracted position towards the extended position. As shown, expansion nut 94 may be moved a predetermined distance along tapered surface 82 of respective engagement member(s) 42 such that the engagement members define a (e.g., enlarged) radius having length 69. Further movement of expansion nut 94 towards first end 18 of housing 14 may enlarge length 69 and movement of the expansion nut towards second end 22 of the housing may reduce length 69. For example, longitudinal movement of actuator 74 towards second end 22 of housing may disengage expansion nut 94 and engagement member 42, thereby allowing the engagement member to move toward the retracted position (e.g., via the biasing member).

In the depicted embodiment, housing 14 may be configured to accommodate a washer 98 on an outer surface thereof. As shown, washer 98 may include a plurality of (e.g., substantially sharp) protrusions 102 configured to engage an outer surface 103 of a cortical wall 104 ("iliac cortical wall") of an ilium bone 105. In this embodiment, at least a portion of the outer surface of (e.g., midsection 26 of) housing 14 may be threaded and configured to receive a locking nut 106. Locking nut 106 may be configured to secure washer 98 against outer surface 103 of iliac cortical wall 104, as discussed in further detail below.

In the depicted embodiment, at least a portion of (e.g., the inner and/or outer surface of) housing 14 comprises a circular cross-section. As shown, at least a portion of midsection 26 is substantially straight. More particularly, at least a portion of housing 14 (e.g., at midsection 26) includes a substantially uniform lateral (e.g., outer) dimension 110 (e.g., an outer diameter, as shown) measured in a direction perpendicular to longitudinal axis 38 of the midsection. Expansion nut 94 and/or shaft 90 may include a (e.g., circular) (e.g., inner and/or outer) cross-section corresponding to the (e.g., circular) (e.g., inner and/or outer) cross-section of housing 14. In the embodiment shown, housing 14 and/or actuator 74 may include any biocompatible suitable material, such as plastic, stainless steel, rubber, titanium, and/or the like.

In the depicted embodiment, bore 66 of housing 14 and actuator 74 may be configured to accommodate and move relative to a guidewire 114 (e.g., such as a Kirschner wire ("K-wire"), Steinmann pin, and/or the like).

Figure 4:
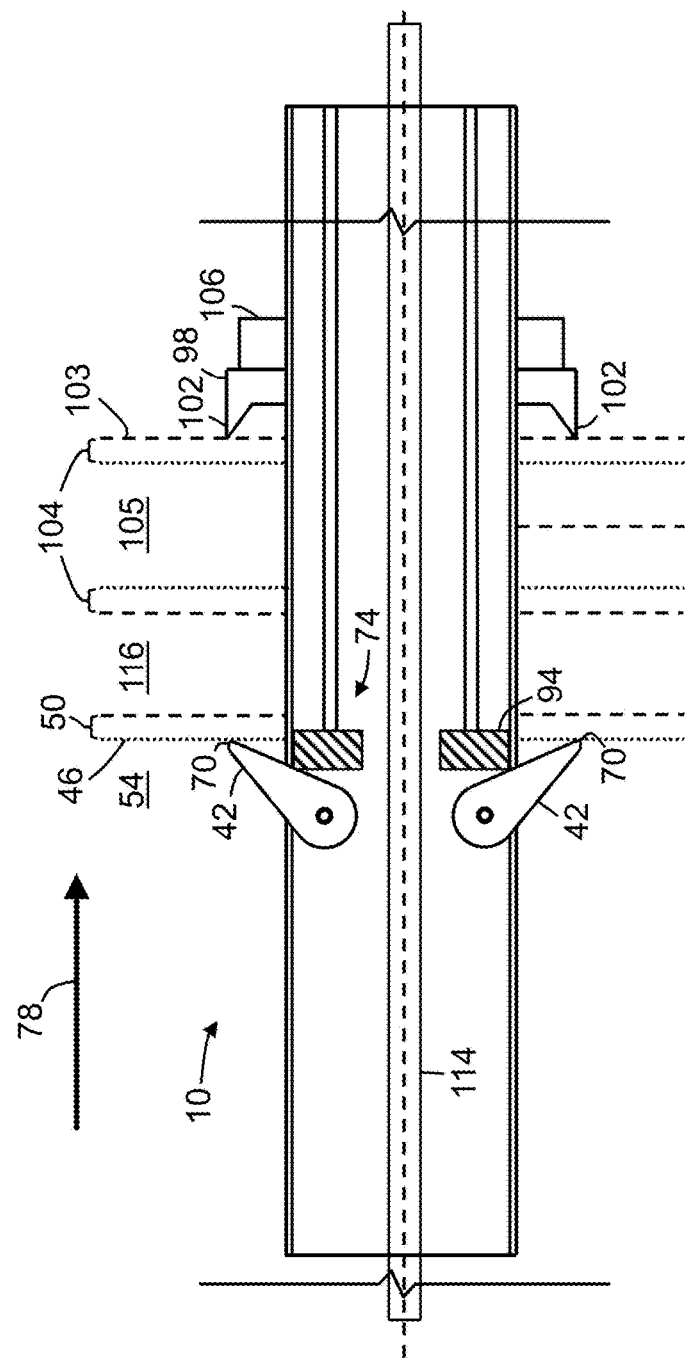

FIGS. 3 and 4 show a schematic view of sacrum 54, ilium 105, and a sacroiliac joint 116 ("SI joint") therebetween. In the depicted embodiment, in operation, guidewire 114 may be inserted in a lateral trajectory across ilium 105 and into sacrum 54. Thereafter, in some embodiments, a space around a guidewire (e.g., 114) may be enlarged using drills, taps, and/or a combination thereof. In some embodiments, in preparation for bone placement, an SI joint (e.g., 116) may be at least partially cleared and/or cleaned using one or more (e.g., angled) curettes.

Next, housing 14 is guided toward SI joint 116 via guidewire 114 and the housing is positioned such that one or more engagement member(s) 42 are longitudinally spaced from inner surface 46 of sacral cortical wall 50, thereby permitting the engagement member(s) to move towards the extended position. Thereafter, actuator 74 may be moved through bore 66 of housing 14 (e.g., using a hollow screw driver guided by guidewire 114) towards first end 18 of the housing such that the actuator engages one or more engagement member(s) 42 and moves the engagement member(s) towards the extended position, as described above. In some embodiments, a housing (e.g., 14) may be moved in a direction (e.g., 78) away from the patient such that a user may confirm secure engagement of one or more engagement member(s) (e.g., 42) with a cortical wall (e.g., 50) of a sacrum (e.g., 54). Next, washer 98 and locking nut 106 may be moved towards first end 18 of housing 14 and the washer may engage outer surface 103 of iliac cortical wall 104. In this embodiment, locking nut 106 may be fastened (e.g., threadedly fastened, using a hollow screw driver) on the outer surface of housing 14, thereby securing washer 98 against outer surface 103 of iliac cortical wall 104. In turn, one or more engagement member(s) 42 of housing 14 are pulled towards washer 98 and against inner surface 46 of sacral cortical wall 50, thereby providing rigid fixation of SI joint 116. In some embodiments, an actuator (e.g., 74) may be removed from the patient after a washer (e.g., 98) and a locking nut (e.g., 106) have been secured against an outer surface (e.g., 103) of an iliac cortical wall (e.g., 104) and/or after confirming secure engagement of one or more engagement member(s) (e.g., 42) with an inner surface (e.g., 46) of a sacral cortical wall (e.g., 50) by moving a housing (e.g., 14) in a direction (e.g., 78) away from the patient. Thereafter, guidewire 114 may be removed.

Figure 5:
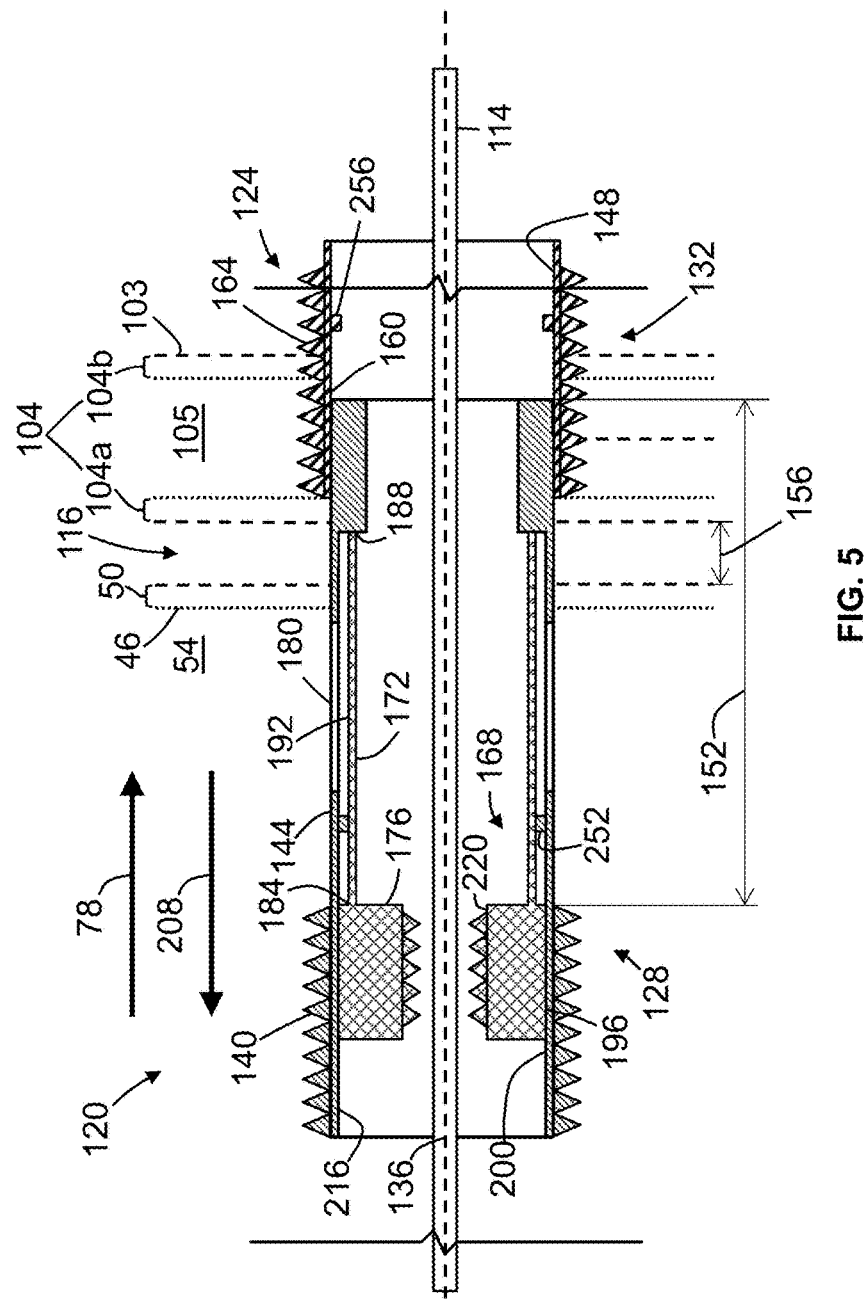
FIG. 5 is a cross-section view of a second embodiment of the present anchor devices, shown with engagement members in a first position and a housing in a first position.
Figure 6:
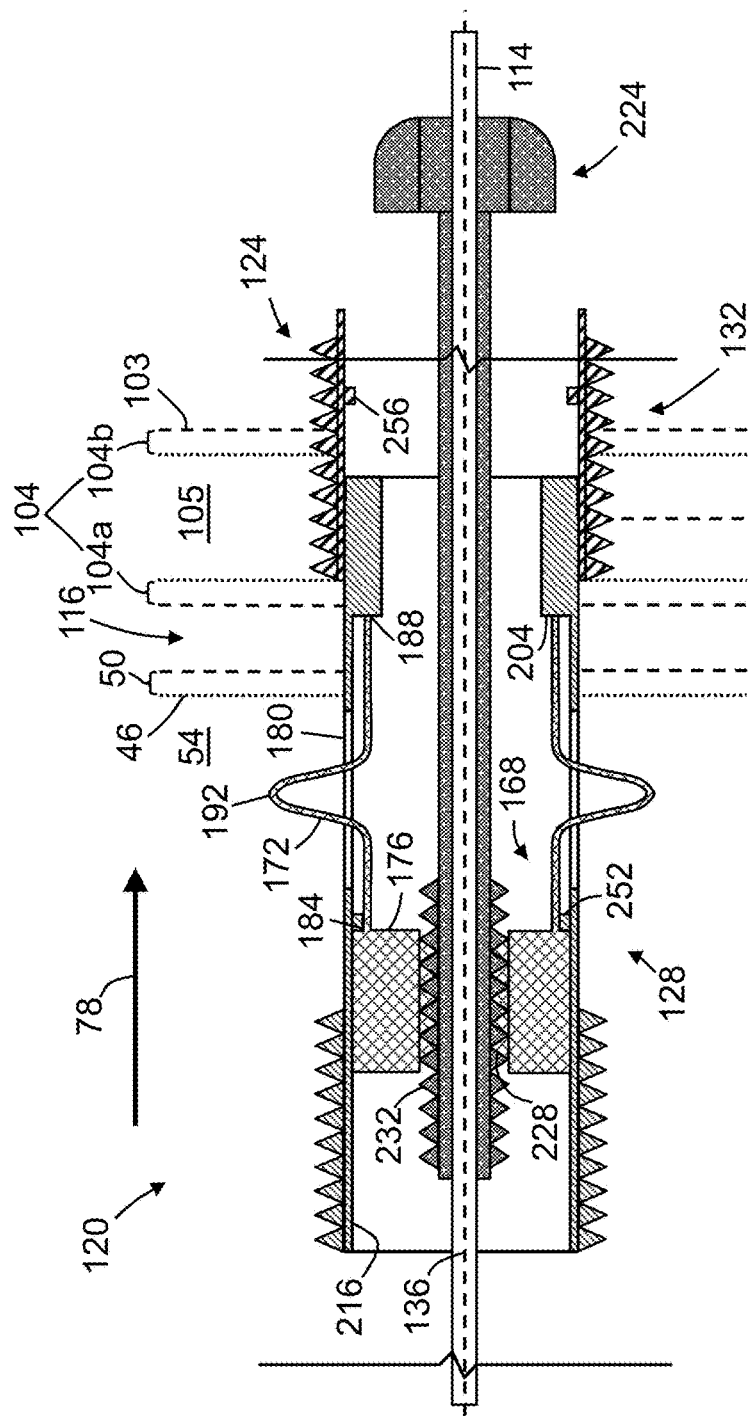
FIG. 6 is a cross-section view of the anchor device of FIG. 5, shown with the engagement members in a second position and an actuator partially disposed in the housing.
Figure 7:
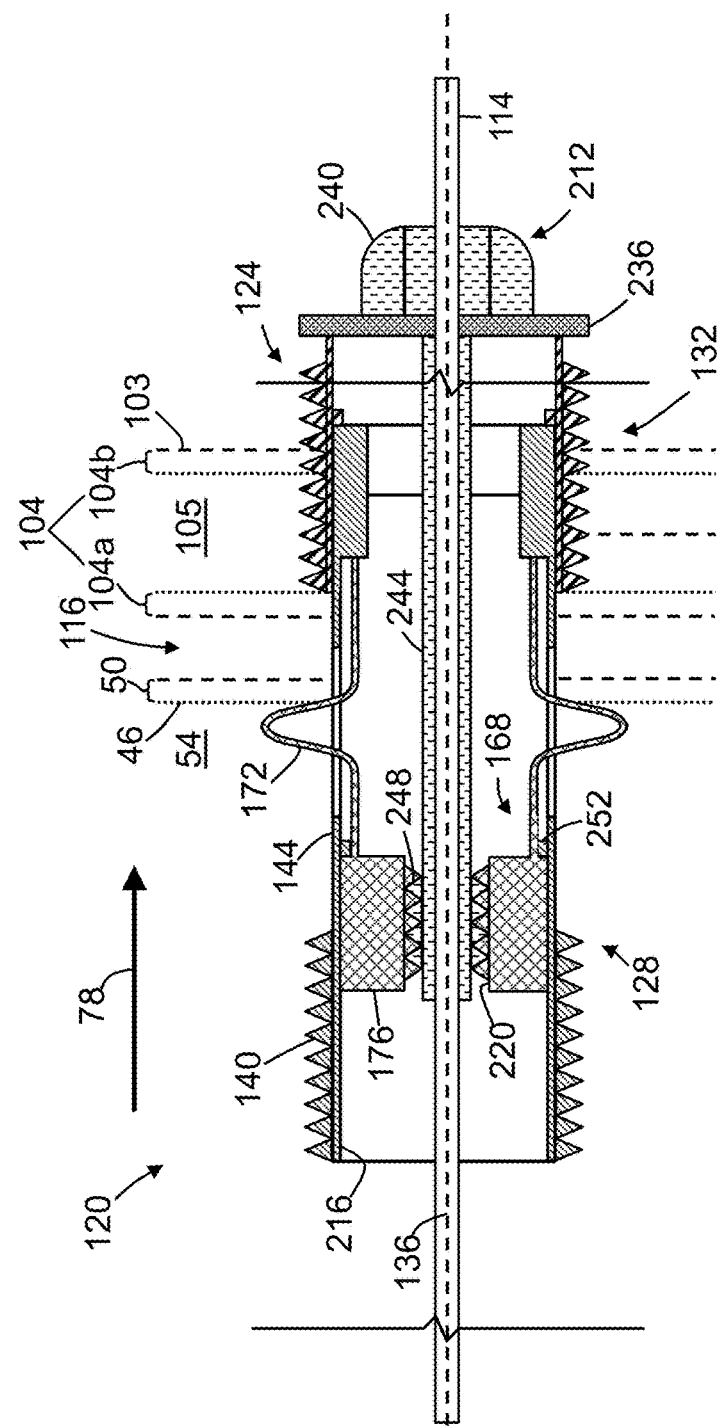
FIG. 7 is a cross-section view of the anchor device of FIG. 5, shown with the housing in a second position and a compression tool partially disposed in the housing.
Figure 8:
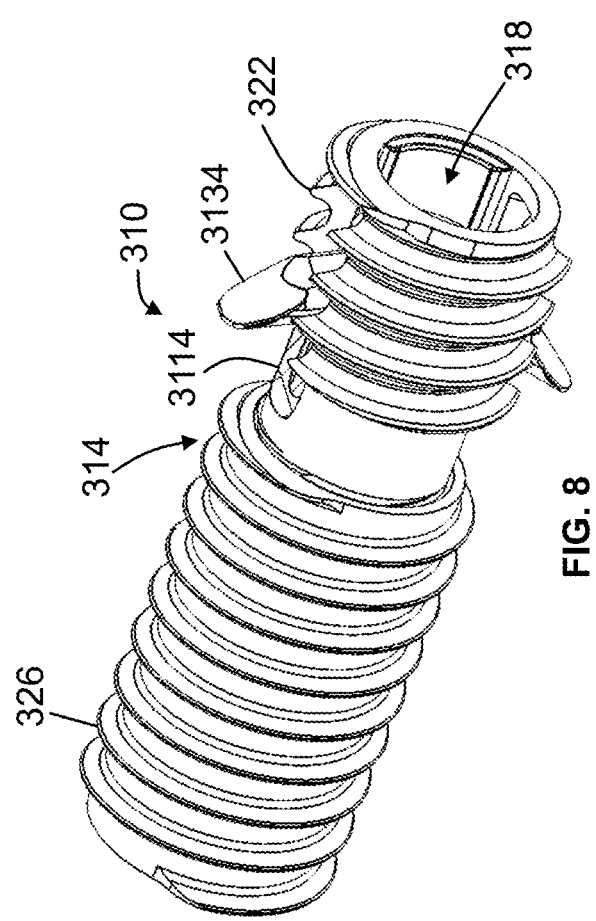
FIG. 8 is a perspective view of a third embodiment of the present anchor devices, shown with engagement members in a first position.

Referring now to FIGS. 5-7, shown therein and designated by the reference numeral 120 is another embodiment of the present anchor devices. As shown, guidewire 114 can be disposed through device 120 and the device can be positioned across SI joint 116 such that the device extends into sacrum 54 and ilium 105. In this embodiment, device 120 includes a housing 124 having an inner anchor 128 movable (e.g., axially and/or rotationally) relative to an outer anchor 132. Housing 124 may be characterized by and described relative to a longitudinal axis 136 extending along a length thereof. As shown, a first portion of inner anchor 128 may include a threaded outer surface 140 configured to be threaded through iliac cortical wall 104 and sacral cortical wall 46. In some embodiments, when an inner anchor (e.g., 128) is threaded through an iliac cortical wall (e.g., 104), a threaded outer surface (e.g., 140) comprises a length such that the threaded outer surface abuts the iliac cortical wall. In some embodiments, an inner anchor (e.g., 128) may include a threaded outer surface (e.g., 140) that extends along a majority of a length of the inner anchor (e.g., along 55, 60, 65, 70, 75, 80, 85, 90, or 95 percent of the length of the inner anchor). In the embodiment shown, a second portion of inner anchor 128 may include a non-threaded outer surface 144 such that the inner anchor is moveable into a bore 148 of outer anchor 132. Non-threaded outer surface 144 of inner anchor 128 may be configured to include a length 152 at least as long as a length 156 of SI joint 116. For example, length 152 may be greater than any one of, or between any two of: 0.8, 1.0, 1.2, 1.4, 1.6, 1.8, 2.0, 2.2, and 2.4 millimeters. As shown, non-threaded outer surface 144 of inner anchor 128 is slidable along an inner surface 160 of outer anchor 132. Outer anchor 132 may include a threaded outer surface 164 configured to be threaded through an outer iliac cortical wall 104b such that axial movement of the outer anchor is thereby restricted. In this embodiment, threaded outer surface 140 of inner anchor 128 may be configured to be timed with threaded outer surface 164 of outer anchor 132 such that a single thread groove is formed through cortical wall 104 of ilium 105 and cortical wall 50 of sacrum 54.

In the depicted embodiment, at least a portion of housing 124 includes a circular cross-section. In some embodiments, a housing (e.g., 124) may include any suitable cross-section shape, such as, for example, square, rectangular, triangular, ovular, and/or the like. In the embodiment shown, housing 124 may include any biocompatible suitable material, such as plastic, stainless steel, rubber, titanium, and/or the like.

In the depicted embodiment, device 120 includes an expandable core 168. At least a portion of expandable core 168 may be (e.g., axially and/or laterally, but not rotationally) moveable relative to housing 124. As shown, expandable core 168 may include one or more engagement member(s) 172 and a base 176. More particularly, in this embodiment, device 120 includes six engagement members 172 and one or more apertures 180 defined in housing 124 and configured to accommodate one or more of the engagement members such that the engagement member(s) can extend through the aperture(s). In some embodiments, a device (e.g., 120) may include any suitable number of engagement member(s) (e.g., 172), such as, for example, any one of, or between any two of: 2, 3, 4, 5, 6, 7, 8, 9, and 10. Engagement member(s) 172 may be configured to be movable from a retracted position to an extended position, where in the extended position one or more of the engagement member(s) may be configured to laterally extend outward relative to longitudinal axis 136 and thereby prevent axial movement of inner anchor 128 in direction 78 across SI joint 116.

In the embodiment shown, engagement member 172 may include a first end 184, a second end 188, and a midsection 192 between the first end and the second end. As shown, first end 184 of engagement member 172 may be unitary with base 176. In some embodiments, a first end (e.g., 184) of an engagement member (e.g., 172) may be coupled to a base (e.g., 176). In the embodiment shown, base 176 and inner anchor 128 may cooperate to inhibit or frustrate axial and/or rotational movement relative to each other. For example, an outer surface 196 of base 176 may be configured to engage an inner surface 200 of inner anchor 128 such that a friction force therebetween holds the base in a first axial position (FIG. 5) and a predetermined axial force (e.g., greater than the friction force) exerted on the base moves the base to a second axial position (FIGS. 6 and 7). In the depicted embodiment, base 176 and inner anchor 128 may cooperate to inhibit rotational movement relative to each other such that one or more engagement member(s) 172 remain circumferentially aligned with a respective aperture 180 in housing 124. For example, as shown, base 176 may include an outer circumferential shape that is rectangular, square, triangular, pentagonal, hexagonal, or otherwise polygonal and inner anchor 128 may include a corresponding inner circumferential shape that is rectangular, square, triangular, pentagonal, hexagonal, or otherwise polygonal. In some embodiments, a base (e.g., 176) and an inner anchor (e.g., 128) may include any appropriate corresponding outer and inner circumferential shape or protrusion, respectively, such that one or more engagement member(s) (e.g., 172) remain circumferentially aligned with a respective aperture (e.g., 180).

In this embodiment, engagement member 172 may be inhibited from moving axially (e.g., in direction 78) in housing 124. For example, second end 188 of engagement member 172 may be configured to engage a shoulder 204 defined by the housing. As shown, shoulder 204 may be defined by inner anchor 128, such as, for example, a portion of the inner anchor 128 extending toward longitudinal axis 136. In some embodiments, a shoulder (e.g., 204) configured to inhibit axial movement of the engagement member (e.g., 172) may be defined by an outer anchor (e.g., 132) of the housing (e.g., 124).

In some embodiments, a first end (e.g., 184) and/or a base (e.g., 176) of an engagement member (e.g., 172) may be coupled to, or unitary with, an inner anchor (e.g., 128) and a second end (e.g., 188) of the engagement member may be coupled to, or unitary with, an outer anchor (e.g., 132) such that relative axial movement between the inner anchor and the outer anchor both laterally extends the engagement member and axially moves the engagement member against an inner surface (e.g., 46) of a sacral cortical wall (e.g., 50). In some embodiments, a second end (e.g., 188) of an engagement member (e.g., 172) may be coupled to, or integrally formed with, one of an inner anchor (e.g., 128) and an outer anchor (e.g., 132) such that axial movement of a first end (e.g., 184) of the engagement member toward the second end laterally extends the engagement member. In some embodiments, a second end (e.g., 188) of an engagement member (e.g., 172) may be coupled to, or integrally formed with a base (e.g., 176) such that axial movement of the base in a direction (e.g., 208), for example, via a compression tool (e.g., 212), laterally extends the engagement member.

As shown, engagement member 172 (e.g., midsection 192) may be at least partially disposed in a bore 216 of inner anchor 128 when the engagement member is in each of the retracted position and extended positions. In the retracted position, engagement member(s) 172 (e.g., midsection 192) may be configured to minimize or avoid engagement with sacral cortical wall 50 and/or iliac cortical wall 104 such that the engagement member does not frustrate insertion of device 120 across SI joint 116. In the extended position, at least a portion of midsection 192 of one or more engagement member(s) 172 is configured to laterally extend through aperture 180 defined by housing 124 such that the one or more engagement member(s) may securely engage inner surface 46 of cortical wall 50 of sacrum 54 and thereby prevent axial movement of inner anchor 128 across SI joint 116. As shown, one or more aperture(s) 180 may be defined by inner anchor 128 of housing 124. In some embodiments, one or more aperture(s) (e.g., 180) may be defined by an outer anchor (e.g., 132) of a housing (e.g., 124) or by a combination of an inner anchor (e.g., 128) and the outer anchor of the housing.

In the embodiment shown, base 176 may be configured to effectuate movement of one or more engagement member(s) 172 from the retracted position to the extended position. For example, base 176 includes an inner surface 220 configured to engage an actuator 224. As shown, at least a portion of inner surface 220 of base 176 may include threads 228 configured to mate with corresponding threads 232 on actuator 224. In this embodiment, rotation of actuator 224 may cause axial movement of base 176 in direction 78 such that first end 184 of engagement member 172 moves axially towards second end 188. In turn, midsection 192 of engagement member 172 may move laterally outward relative to longitudinal axis 136. In some embodiments, a base (e.g., 176) may engage an actuator (e.g., 224) in any other suitable manner such that the actuator causes axial movement of the base relative to a housing (e.g., 124). In some embodiments, an actuator (e.g., 224) may be configured to directly engage one or more engagement member(s) (e.g., 172) such that a first end (e.g., 184) of one or more engagement member(s) move axially towards a second end (e.g., 188) thereof and, in turn, a midsection (e.g., 192) of one or more of the engagement member(s) moves laterally outward relative to a longitudinal axis (e.g., 136).

In the embodiment shown, engagement member(s) 172 may include a deformable material configured to deform when the engagement member(s) move from the retracted position to the extended position. In this embodiment, deformable material of engagement member 172 may include commercially pure (CP) titanium. In some embodiments, a deformable material of an engagement member (e.g., 172) may include any appropriate deformable material, such as, for example, plastic, steel, and/or the like.

In use, device 120 may be guided toward SI joint 116 via guidewire 114. More particularly, device 120 may be guided on guidewire 114 via a tool which holds inner anchor 128, outer anchor 132 axially fixed relative to each other. As shown, inner anchor 128 may be threaded through iliac cortical wall 104 and/or sacral cortical wall 50 such that a majority of each aperture 180 is positioned in sacrum 54, thereby permitting engagement member(s) to move towards the extended position in the sacrum. Outer anchor 132 may be threaded into outer iliac cortical wall 104b and/or may be configured to abut an inner iliac cortical wall 104a. Next, expandable core 168 may be guided into housing 124 (e.g., via guidewire 114) such that engagement member(s) 172 are substantially axially aligned with aperture(s) 180 of the housing. In some embodiments, an expandable core (e.g., 168) may be disposed within a housing (e.g., 124) of a device (e.g., 120) when the device is positioned across an SI joint (e.g., 116).

Next, actuator 224 may be used to move one or more engagement member(s) 172 from the retracted position to the extended position, as described herein. Thereafter, actuator 224 may be removed from device 120. Inner anchor 128 may then be axially moved relative to outer anchor 132 such that engagement member(s) 172 securely engage inner surface 46 of sacral cortical wall 50. In some embodiments, bone graft may be inserted into SI joint 116 in any manner known in the art. As shown, a compression tool 212 and a washer 236 may urge inner anchor 128, and therefore engagement member(s) 172, toward sacral cortical wall 50. Compression tool 212 may comprise any suitable device configured to urge inner anchor 128 toward sacral cortical wall 50. For example, compression tool 212 may include a head 240, a shaft 244, and threads 248 on the shaft configured to engage threads 228 on base 176. In this embodiment, compression tool 212 may include a hex screw. By fastening compression tool 212, an axial force (e.g., greater than the axial force required to move engagement member(s) 172 from the retracted position to the extended position) is exerted on inner anchor 128 (e.g., via expandable core 168) such that the inner anchor moves axially relative to outer core 132 in direction 78. In turn, midsection 192 of engagement member(s) 172 engages inner surface 46 of sacral cortical wall 50, thereby preventing movement of inner anchor across SI joint 116. Thereafter, guidewire 114 may be removed from device 120.

In the embodiment shown, when one or more engagement member(s) 172 move from the retracted position to the extended position, inner anchor 128 and outer anchor 132 may remain axially fixed relative to each other. More particularly, an anchor friction force between an outer surface of inner anchor 128 and inner surface of outer anchor 132 may be configured to hold the inner and outer anchor in a first axial position (FIG. 5) and a predetermined axial force (e.g., greater than the friction force) exerted on the inner anchor (e.g., via compression tool 212) may move the inner anchor to a second axial position relative to outer anchor (FIG. 7). In some embodiments, a compression tool (e.g., 212) may be omitted and an actuator (e.g., 224) may be used both to move one or more engagement member(s) (e.g., 172) from a retracted position to an extended position and to move an inner anchor (e.g., 128) from a first axial position to a second axial position.

Some embodiments of the present devices (e.g., 120) may be configured to reduce and/or avoid the creation and/or propagation of fractures in sacral cortical wall 50 and iliac cortical wall 104. For example, in the embodiment shown, inner anchor 128 includes a protrusion 252 on inner surface 200, where the protrusion is configured to limit the overall axial movement of base 176 in direction 78, thereby limiting the overall lateral extension of one or more engagement member(s) 172 in the extended position. As such, engagement member(s) 172 minimize a risk of damaging sacral cortical wall 50 by overextending in the lateral direction. For further example, in some embodiments, a device (e.g., 120) may include one or more aperture(s) (e.g., 180) having a longitudinal dimension configured to limit the lateral extension of one or more respective engagement member(s) (e.g., 172) extending therethrough, thereby limiting the overall lateral extension of the one or more engagement member(s) in the extended position. For yet further example, in the embodiment shown, device 120 may include a protrusion 256 configured to limit relative movement between inner anchor 128 and outer anchor 132, thereby limiting the axial force exerted by engagement member(s) on sacral cortical wall 50. For yet further example, in some embodiments, a compression tool (e.g., 212) may include a head (e.g., 240) having a material configured to strip when a predetermined axial force is applied to inner surface 46 of sacral cortical wall 50.

Referring now to FIGS. 8-16, shown therein and designated by the reference numeral 310 is one embodiment of the present anchor devices. In the embodiment shown, device 310 includes an elongated housing 314 having a channel 318 extending therethrough. In the depicted embodiment, housing 314 comprises an inner anchor 322 movable (e.g., axially and/or rotationally) relative to an outer anchor 326. In this embodiment, housing 314 may be characterized by and described relative to a longitudinal axis 330 extending along a length thereof.

In the embodiment shown, inner anchor 322 may include a first end 334, a second end 338, and a channel 342 extending between the first end and the second end. As shown, inner anchor 322 may include a first threaded outer surface 346 and a second threaded outer surface 350 axially spaced from the first threaded outer surface. Referring to FIG. 9, shown therein is device 310, a sacrum bone 354, an iliac bone 358, and a sacroiliac joint 362 ("SI joint") between the sacrum and the ilium. In this embodiment, first threaded outer surface 346 may be configured to be threaded through an outer cortical wall 366a and an inner cortical wall 366b of iliac bone 358 ("iliac cortical wall") and/or an outer cortical wall 370 of sacrum bone 354 ("sacral cortical wall") and second threaded outer surface 350 may be configured to be threaded with a corresponding threaded inner surface 374 of outer anchor 326. In the embodiment shown, inner anchor 322 may include a non-threaded outer surface 378 between first threaded outer surface 346 and second threaded outer surface 350. In the depicted embodiment, non-threaded outer surface 378 of inner anchor 322 may be configured to include an axial length 382 at least as long as a length 386 of SI joint 362. For example, in this embodiment, length 382 may be greater than any one of, or between any two of: 0.8, 1.0, 1.2, 1.4, 1.6, 1.8, 2.0, 2.2, and 2.4 millimeters.

In the embodiment shown, outer anchor 326 may include a first end 390, a second end 394, and a channel 398 extending between the first end and the second end. As shown, first end 334 of inner anchor 322 may be at least partially disposed in channel 398 of outer anchor 326. In the depicted embodiment, at least a portion of outer anchor 326 may include a threaded outer surface 3102 configured to be threaded into outer iliac cortical wall 366a such that axial (e.g., translational) movement of the outer anchor relative to the outer iliac cortical wall is thereby restricted. In this embodiment, threaded outer surface 3102 of outer anchor 326 may be configured to be timed with first threaded outer surface 346 of inner anchor 322 such that, for example, a single thread groove is formed in iliac cortical wall 366a, 366b and/or sacral cortical wall 370 when device 310 is positioned across SI joint 362. In the embodiment shown, threaded inner surface 374 of outer anchor 326 and second threaded outer surface 350 of inner anchor 322 may include a pitch 3106 greater than a pitch 3110 of threaded outer surface 3102 of outer anchor 326 and first threaded outer surface 346 of inner anchor 322 (e.g., FIG. 23). For example, in this embodiment, pitch 3106 may be 1, 5, 10, 15, 20, 25, 30, 35 percent or more greater than pitch 3110. In the depicted embodiment, threaded inner surface 374 of outer anchor 326 and/or second threaded outer surface 350 of inner anchor 322 may include a single-start thread. In some embodiments (e.g., 310), a threaded inner surface (e.g., 374) of an outer anchor (e.g., 326) and a second threaded outer surface (e.g., 350) of an inner anchor (e.g., 322) may include any appropriate thread start, such as, for example, a double-start thread or a triple-start thread. As shown, threaded outer surface 3102 of outer anchor 326 and/or first threaded outer surface 346 of inner anchor 322 may include a single-start thread. In some embodiments, a threaded outer surface (e.g., 3102) of an outer anchor (e.g., 326) and/or a first threaded outer surface (e.g., 346) of an inner anchor (e.g., 322) may include any appropriate thread start, such as, for example, a double-start thread or a triple-start thread.

In the depicted embodiment, at least a portion of housing 314 includes a circular cross-section. In some embodiments (e.g., 310), a housing (e.g., 314) may include any suitable cross-section shape, such as, for example, square, rectangular, triangular, ovular, and/or the like. In the embodiment shown, housing 314 may include any suitable biocompatible material, such as plastic, stainless steel, rubber, titanium, and/or the like.

In the embodiment shown, housing 314 may be configured to include one or more apertures 3114 (e.g., two apertures, as shown). More specifically, in this embodiment, one or more aperture(s) 3114 may be defined by inner anchor 322 of housing 314. In some embodiments (e.g., 310), one or more aperture(s) (e.g., 3114) may be defined by an outer anchor (e.g., 326) of a housing (e.g., 314) or by a combination of an inner anchor (e.g., 322) and the outer anchor of the housing.

In this embodiment, device 310 may include a carriage assembly 3118. As shown, carriage assembly 3118 may include a carriage housing 3122, an actuator 3126, a compression member 3130, and one or more engagement member(s) 3134 (e.g., two engagement members, as shown) coupled to the carriage housing.

In the depicted embodiment, carriage housing 3122 may include one or more carriage apertures 3138 (e.g., two carriage apertures, as shown) corresponding to apertures 3114 of housing 314 (e.g., of inner anchor 322, more particularly). In this embodiment, carriage housing 3122 and inner anchor 322 may be configured to cooperate to prevent rotation of the carriage housing relative to the inner anchor when the carriage housing is disposed in channel 342 of the inner anchor. More specifically, carriage housing 3122 and inner anchor 322 may cooperate to prevent circumferential misalignment between aperture(s) 3114 of housing 314 (e.g., inner anchor 322) and carriage aperture(s) 3138 of carriage housing 3122. For example, in the embodiment shown, an outer surface 3142 of carriage housing 3122 may include one or more first protrusion(s) 3146 (e.g., two first protrusions, as shown) extending radially outward relative to longitudinal axis 330 and configured to be keyed into corresponding alignment slot(s) 3150 (e.g., two alignment slots, as shown) defined by an inner surface 3154 of inner anchor 322. In the depicted embodiment, carriage housing 3122 and inner anchor 322 may (e.g., also) be configured to cooperate to prevent axial misalignment between aperture(s) 3114 of housing 314 and carriage aperture(s) 3138 of carriage housing 3122 when the carriage housing is disposed in channel 342 of the inner anchor. For example, in this embodiment, outer surface 3142 of carriage housing 3122 may include one or more second protrusion(s) 3158 (e.g., two second protrusions, as shown) extending radially outward relative to longitudinal axis 330 and configured to engage a respective shoulder 3162 defined by inner surface 3154 of inner anchor 322 (e.g., at a predetermined distance from first end 334 of the inner anchor such that, when the one or more second protrusion(s) engage the corresponding shoulder(s) 3162, one or more engagement member(s) 3134 are substantially axially aligned with respective carriage aperture(s) 3138 of carriage housing 3122 and aperture(s) 3114 of housing 314). In this embodiment, one or more shoulder(s) 3162 may be configured to inhibit further axial movement of carriage housing 3122 relative to inner anchor 322 (e.g., inhibit axial movement towards second end 338 of the inner anchor).

In the depicted embodiment, one or more engagement member(s) 3134 may be movable between a retracted position and an extended position. In the retracted position, one or more engagement member(s) 3134 may be configured to extend a first distance 3166 from longitudinal axis 330. In the extended position, one or more engagement member(s) 3134 may be configured to extend a second distance 3170 from longitudinal axis 330, where second distance 3170 is greater than first distance 3166. More particularly, in this embodiment, one or more engagement member(s) 3134 may be configured to extend through respective carriage aperture(s) 3138 of carriage housing 3122 and respective aperture(s) 3114 of housing 314 when the one or more engagement member(s) are in the extended position. Further, in the depicted embodiment, one or more engagement member(s) 3134 may be configured to extend into the cancellous bone of sacrum 354 (e.g., and securely engage an inner surface 3174 of sacral cortical wall 370) when the one or more engagement member(s) are in the extended position. In the depicted embodiment, when one or more engagement member(s) 3134 are in the retracted position, the one or more engagement member(s) may be configured to be substantially flush with outer surface 3142 of carriage housing 3122. In some embodiments (e.g., 310), one or more engagement member(s) (e.g., 3134) may be configured to be biased toward the retracted position (e.g., by a biasing member such as, for example, a spring and/or the like).

In the embodiment shown, a respective first end 3178 of one or more engagement member(s) 3134 may be coupled to a hinge 3182 disposed in a channel 3186 of carriage housing 3122 and at least one of the one or more engagement member(s) may rotatable between the retracted position and the extended position via the hinge. In this embodiment, one or more engagement member(s) 3134 may be coupled with hinge 3182 such that the engagement member moves uniaxially, biaxially, or multiaxially relative to the hinge, thereby allowing the engagement member to adjust to irregularities and variable angles of inner surface 3174 of sacral cortical wall 370. In the depicted embodiment, one or more engagement member(s) 3134 include a shoulder 3190 at first end 3178. As shown, shoulder 3190 of one engagement member 3134 may engage shoulder 3190 of another engagement member 3134 when one or more of the engagement member(s) are in the extended position, as shown, for example, in FIG. 12. In this configuration, movement of one respective engagement member 3134 (e.g., in a clockwise direction 3194 about hinge 3182) may cause another respective engagement member to move (e.g., in the clockwise direction about the hinge) and vice versa.

In the depicted embodiment, one or more engagement member(s) 3134 may include any appropriate shape such that, when the engagement member is the extended position, a second end 3198 of the engagement member is configured to securely engage inner surface 3174 of sacral cortical wall 370 and prevent removal of housing 314 (e.g., of inner anchor 322, more particularly) from sacrum 354 (e.g., prevent translational movement in a direction 3202). As shown, one or more engagement member(s) 3134 may include an inwardly-facing tapered surface 3206. For example, in this embodiment, one or more engagement member(s) 3134 include a thickness (e.g., measured in a direction perpendicular to longitudinal axis 330 when the engagement member is flush with outer surface 3142 of carriage housing 3122, as shown in FIGS. 16 and 19) configured to decrease from first end 3178 of the engagement member to second end 3198 of the engagement member. In the embodiment shown, second end 3198 of one or more engagement member(s) 3134 can converge to a point such that the second end engages inner surface 3174 of sacral cortical wall 370 (e.g., without penetrating the sacral cortical wall) to secure device 310 in sacrum 354. In some embodiments (e.g., 310), a second end (e.g., 3198) of one or more engagement member(s) (e.g., 3134) may include any suitable shape such that the second end engages an inner surface (e.g., 3174) of a sacral cortical wall (e.g., 370) (e.g., without penetrating the sacral cortical wall) to secure a device (e.g., 310) in a sacrum (e.g., 354).

In this embodiment, actuator 3126 and compression member 3130 each comprise a screw. In the depicted embodiment, carriage housing 3122 may include a threaded inner surface 3210 configured to mate with a threaded surface 3214 of actuator 3126 and a threaded surface 3218 of compression member 3130. In this embodiment, actuator 3126 and compression member 3130 include a respective cap portion 3222, 3226 having grooves configured to mate with an expansion member (e.g., insertable into and out of channel 318 of housing 314). As shown, cap portion 3226 of compression member 3130 may include a shoulder 3230 configured to engage a corresponding shoulder 3234 defined by inner anchor 322. In this embodiment, shoulder 3234 may be configured to inhibit axial movement of compression member 3130 relative to carriage housing 3122 (e.g., inhibit axial movement towards second end 338 of the inner anchor) when the shoulder of the compression member engages the shoulder of the inner anchor.

In the depicted embodiment, actuator 3126 may be configured to effectuate movement of one or more engagement member(s) 3134 between the retracted position and the extended position. More specifically, in this embodiment, actuator 3126 may be longitudinally movable relative to one or more engagement member(s) 3134 (e.g., by threading the actuator along threaded inner surface 3210 of carriage housing 3122) such that the actuator engages (e.g., tapered surface 3206 of) the one or more engagement member(s). For example, in the depicted embodiment, a tip of expansion member may be inserted into cap 3222 of actuator 3126 and rotated (e.g., in a clockwise direction 3238, as shown, for example, from the perspective of FIG. 10) such that the actuator moves axially relative to carriage housing 3122 toward second end 338 of inner anchor 322 (e.g., while the carriage housing remains axially fixed due to engagement between shoulder 3162 and second protrusion 3158). In this embodiment, axial movement of actuator 3126 relative to carriage housing 3122 may engage the actuator with tapered surface 3206 of one or more engagement member(s) 3134. Additional axial movement of actuator 3126 relative to carriage housing 3122 (e.g., towards second end 338 of inner anchor 322) may move the actuator axially along tapered surface 3206 of one or more engagement member(s) 3134, thereby moving (e.g., rotating) the one or more engagement member(s) from the retracted position toward the extended position. In the depicted embodiment, actuator 3126 may urge one or more engagement members 3134 toward the extended position. In some embodiments, an actuator (e.g., 3126) may urge one or more engagement members (e.g., 3134) toward the extended position until a shoulder (e.g., 3190) of one engagement member engages the shoulder of another engagement member. In some embodiments, the expansion member, and thus actuator 3126, may be rotated (e.g., in a counter clockwise direction 3242, as shown, for example, from the perspective of FIG. 10) such that the actuator moves axially relative to carriage housing 3122 toward first end 334 of inner anchor 322. As a result, in some embodiments, an actuator (e.g., 3126) may disengage one or more engagement member(s) (e.g., 3134), thereby allowing the one or more engagement member(s) to move toward a retracted position (e.g., via a biasing force provided by, for example, a spring).

In the embodiment shown, compression member 3130 may be configured to move carriage housing 3122 toward first end 334 of inner anchor 322. As shown, compression member 3130 may be at least partially disposed in channel 342 of inner anchor 322 and threaded with threaded inner surface 3210 of carriage housing 3122. In the depicted embodiment, compression member 3130 may be configured to engage shoulder 3234 defined by inner anchor 322 such that axial movement toward second end 338 of the inner anchor 322 is inhibited when the shoulder of the compression member engages the shoulder of the inner anchor. In this embodiment, rotation of compression member 3130 (e.g., after the compression member engages shoulder 3234) may cause carriage housing 3122 to move toward first end 334 of inner anchor 322. For example, in the embodiment shown, when one or more engagement member(s) 3134 are in the extended position and the one or more engagement member(s) are disposed in sacrum 354, movement of carriage housing 3122 toward first end 334 of inner anchor 322 may urge the one or more engagement member(s) against inner surface 3174 of sacral cortical wall 370, thereby preventing removal of the device from the sacrum. In this embodiment, urging one or more engagement members 3134 (e.g., by movement of carriage housing 3122 toward first end 334 of inner anchor 332) against inner surface 3174 of sacral cortical wall 370 may cause engagement between a shoulder 3190 of one engagement member and a shoulder 3190 of another engagement member, thereby restricting further rotational movement of the engagement members (e.g., relative to each other) about pin 3182.

In some embodiments (e.g., 310), an actuator (e.g., 3126) and a compression member (e.g., 3130) may be integrally formed, and may comprise, for example, a single screw. In the embodiment shown, one or more components of carriage assembly 3118 and/or the expansion member may include any suitable biocompatible material, such as plastic, stainless steel, rubber, titanium, and/or the like.

In the depicted embodiment, channel 318 of housing 314 (e.g., comprising channel 398 of outer anchor 326 and channel 342 of inner anchor 322) may be configured to accommodate and move relative to a guidewire (e.g., such as a Kirschner wire ("K-wire"), Steinmann pin, and/or the like). In the depicted embodiment, in operation, the guidewire may be inserted in a lateral trajectory across ilium 358 and into sacrum 354. Thereafter, in some embodiments, a space around a guidewire may be enlarged using drills, taps, a combination thereof, and/or the like. In some embodiments, in preparation for bone placement, an SI joint (e.g., 362) may be at least partially cleared and/or cleaned using one or more (e.g., angled) curettes.

Next, housing 314 may be guided toward SI joint 362 via the guidewire and the housing may be positioned such that a majority of an axial length 244 of one or more apertures 3114 is positioned in sacrum 354 (e.g., thereby allowing one or more engagement member(s) 3134 to move into the extended position in sacrum 354, as described herein). As shown, housing 314 (e.g., inner anchor 322, more particularly) may be positioned across SI joint 362 such that outer anchor 326 is threaded into outer iliac cortical wall 366a. In the depicted embodiment, housing 314 (e.g., inner anchor 322, more particularly) may be positioned across SI joint 362 such that a first end 3246 of first threaded outer surface 346 of inner anchor 322 is configured to abut inner surface 3174 of sacral cortical wall 370. Thereafter, a cannula may be securely coupled to first end 390 of outer anchor 326 (e.g., by a key lock). Next, carriage assembly 3118 may be axially guided through the cannula toward second end 338 of inner anchor 322. For example, in this embodiment, carriage housing 3122 may be urged through the cannula and into housing 314 (e.g., into inner anchor 322, more particularly) by the expansion member. In the embodiment shown, axial movement of carriage housing 3122 into inner anchor 322 may continue until the carriage housing engages shoulder 3162, thereby axially aligning one or more engagement member(s) 3134 with respective aperture(s) 3114 of housing 314. Thereafter, actuator 3126 may be guided through the cannula and into housing 314 (e.g., by the expansion member) such that the actuator engages threaded inner surface 3210 of carriage housing 3122. Next, in this embodiment, the expansion member may move (e.g., thread) actuator 3126 into carriage housing 3122 such that the actuator moves one or more engagement member(s) 3134 from the retracted position to the extended position, as described herein. The expansion member may be subsequently removed and compression member 3130 may be guided through the cannula and into housing 314 toward second end 338 of inner anchor 322 (e.g., by the expansion member) such that the compression member engages threaded inner surface 3210 of carriage housing 3122. Thereafter, the expansion member may move (e.g., thread) compression member 3130 into carriage housing 3122. In this embodiment, axial movement of compression member 3130 into carriage housing 3122 may continue until the compression member engages shoulder 3234 of inner anchor 322. Thereafter, in the depicted embodiment, axial movement of compression member 3130 toward second end 338 of inner anchor 322 is inhibited and the compression member may continue to be rotated (e.g., by the expansion member) such that carriage housing 3122 may move toward first end 334 of inner anchor 322. In turn, one or more engagement member(s) 3134, which remain in the extended position (e.g., due to engagement with actuator 3126), may be urged against inner surface 3174 of sacral cortical wall 370, thereby securing device 310 across SI joint 362. In some embodiments, bone graft may be inserted into SI joint 362 in any manner known to those having ordinary skill in the art. In the depicted embodiment, inner anchor 322 may be axially moved relative to outer anchor 326 such that one or more engagement member(s) 3134 securely engage inner surface 3174 of sacral cortical wall 370. For example, the embodiment shown, when one or more engagement member(s) 3134 engage inner surface 3174 of sacral cortical wall 370, inner anchor 322 may be inhibited from rotational movement. As a result, in this embodiment, outer anchor 326 may be rotated relative to inner anchor 322. By rotating outer anchor 326 relative to inner anchor 322, an axial length 3250 between threaded outer surface 3102 of the outer anchor and first threaded outer surface 346 of the inner anchor may be reduced, thereby resulting in a compression force across SI joint 362. For example, in this embodiment, due to the relative difference in length between pitch 3106 and pitch 3110, outer anchor 326 may move (e.g., be threaded) a first predetermined axial distance into outer iliac cortical wall 366a (e.g., in a direction 3254) and, in turn, inner anchor 322 may move (e.g., be threaded) a second predetermined distance relative to the outer anchor (e.g., in a direction 3202), thereby exerting a compressive force on inner surface 3174 of inner sacral cortical wall 370.

Some elements of the present devices (e.g., 10, 120, 310) may be configured in different sizes to accommodate a wide variety of patients. For example, a threaded portion (e.g., 140, 346) of an inner anchor (e.g., 128, 322) may be configured to include any appropriate length (e.g., 3258), such as, for example, any one of, or between any two of: 10, 15, 20, 25, 30, 35, 40, 45, 50, 55, 60, 65, 70, 75, 80, 85, 90, 95, and 100 millimeters. For further example, a threaded portion (e.g., 164, 3102) of an outer anchor (e.g., 132, 326) may be configured to include any appropriate length (e.g., 3262) such as, for example, any one of, or between any two of: 10, 12, 14, 16, 18, 20, 22, 24, 26, 28, 30, 32, 34, 36, 38, and 40 millimeters. In some embodiments, a kit may include one or more inner anchor(s) (e.g., 128, 322) having a length as described herein and one or more outer anchor(s) (e.g., 132, 326) having a length described herein.

The above-described embodiments include the benefits of provide strong constructs that can sustain the weight of the patient's body, resist rotational and translational forces across the SI joint, promote sacroiliac joint fusion over time, and/or take advantage of the sacral cortical layer to resist pull-out. Furthermore, the above-described embodiments include the benefit of a reduced overall outer diameter of the device such that multiple devices may be placed closer together and such that the incision needed to insert the device is minimized.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and devices are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. A method of using an anchor device to stabilize a sacroiliac joint, comprising
positioning an anchor device across a sacroiliac joint (SI joint) such that the device at least partially extends into a sacrum and an ilium, where the anchor device includes:
a housing having:
a bore; and
one or more apertures; and
one or more engagement members at least partially disposed in the bore of the housing, where at least one of the one or more engagement members is movable between a retracted position and an extended position such that, when the at least one of the one or more engagement members is in the extended position, the at least one of the one or more engagement members extends through at least one of the one or more apertures;
moving an actuator in the bore of the housing toward the one or more engagement members; and
engaging the actuator with at least one of the one or more engagement members, thereby moving the at least one of the one or more engagement members from the retracted position to the extended position;
wherein, when the actuator engages the at least one of the one or more engagement members, the engagement member is longitudinally spaced from the cortical wall of the sacrum by a distance such that the engagement member is movable to the extended position within the cancellous bone of the sacrum.

2. The method of claim 1, where the at least one of the one or more engagement members is configured to taper from a first end to a second end, and where the second end is configured to engage the cortical wall of the sacrum.

3. The method of claim 2, where engaging the actuator with the at least one of the one or more engagement members includes engaging the actuator with a tapered surface of the at least one of the one or more engagement members.

4. The method of claim 1, where moving the at least one of the one or more engagement members from the retracted position to the extended position includes deforming the at least one of the one or more engagement members.

5. The method of claim 1, wherein the housing has a threaded outer surface.

6. The method of claim 5, where the housing comprises:
a first anchor having the threaded outer surface and a threaded inner surface;
a second anchor movable relative to the first anchor, where the second anchor includes a threaded outer surface configured to mate with the threaded inner surface of the first anchor, where a pitch of the threaded inner surface of the first anchor is greater than a pitch of the threaded outer surface of the first anchor; and
wherein the method comprises:
axially and/or rotationally moving the first anchor relative to the second anchor to urge the at least one of the one or more engagement members against the cortical wall of the sacrum.

7. The method of claim 1, wherein axial and/or radial movement of the at least one of the one or more engagement members relative to the housing causes the SI joint to compress.

* * * * *